United States Patent [19]

Machida

[11] 4,311,142
[45] Jan. 19, 1982

[54] DEVICE FOR DETECTING A LEAK OF LASER

[75] Inventor: Haruhiko Machida, Tokyo, Japan

[73] Assignee: Machida Endoscope Co., Ltd., Tokyo, Japan

[21] Appl. No.: 965,160

[22] Filed: Nov. 30, 1978

[30] Foreign Application Priority Data

Dec. 29, 1977 [JP] Japan .................. 52-176201[U]

[51] Int. Cl.³ .......................................... A61B 17/00
[52] U.S. Cl. .................. 128/303.1; 128/395; 219/121 LB; 340/557
[58] Field of Search .................. 128/303.1, 172.1, 362, 128/395, 397, 398; 33/DIG. 21; 350/96.29, 96.26; 219/121 LM, 121 L, 121 LA, 121 LB, 121 LZ; 324/52, 65 R; 340/595, 600, 557, 540, 506, 380; 250/199

[56] References Cited

U.S. PATENT DOCUMENTS

| | | | |
|---|---|---|---|
| 3,098,116 | 7/1963 | Jore et al. | 219/221 X |
| 3,208,342 | 9/1965 | Nethercot, Jr. | 350/96.29 |
| 3,445,666 | 5/1969 | Snaper | 350/96.29 X |
| 3,588,776 | 6/1971 | Horwinski | 340/595 X |
| 3,699,649 | 10/1972 | McWilliams | 324/65 R X |
| 3,700,900 | 10/1972 | Herleikson | 250/199 |
| 3,721,898 | 3/1973 | Dragoumis et al. | 324/65 R |
| 3,981,592 | 9/1976 | Williams | 250/199 X |
| 4,000,416 | 12/1976 | Goell | 340/380 X |
| 4,002,896 | 1/1977 | Davies et al. | 250/199 |
| 4,041,771 | 8/1977 | Allan et al. | 340/595 |
| 4,070,091 | 1/1978 | Taylor et al. | 350/96.31 |
| 4,144,530 | 3/1979 | Redfern | 250/199 X |

*Primary Examiner*—Robert W. Michell
*Assistant Examiner*—Arthur S. Rose
*Attorney, Agent, or Firm*—Berger & Palmer

[57] ABSTRACT

The present invention discloses a device for detecting a laser leak for electrically detecting a leakage of laser beam due to snapping of the laser guide which is provided for guiding the laser beam to a desired position. A wire or a conductor which is connected to a detector is provided at the circumference of an optical fiber or a coating material of the laser guide. The snapping of the wire by melting or by the variation of the resistance due to raised temperature or by short-circuit of the wire on account of a dielectric break-down of the coated material is electrically detected by the detector. Thus, leakage of the laser beam from the laser guide is strictly detected to secure the safety of an apparatus and an operator.

7 Claims, 9 Drawing Figures

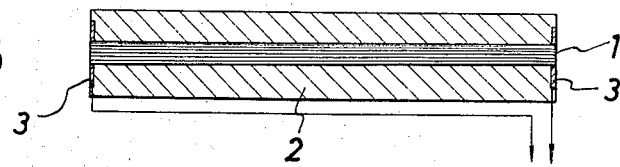
FIG. 6
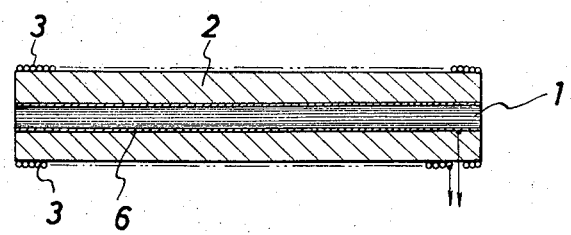
FIG. 7
FIG. 8
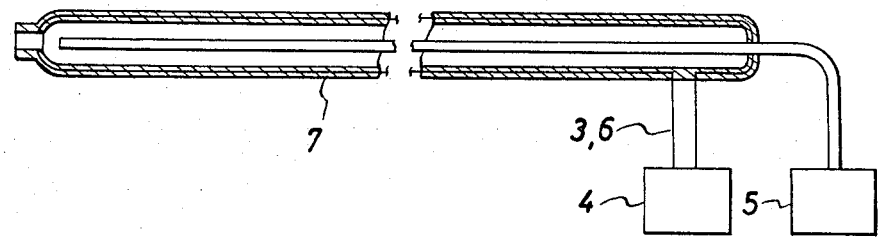
FIG. 9
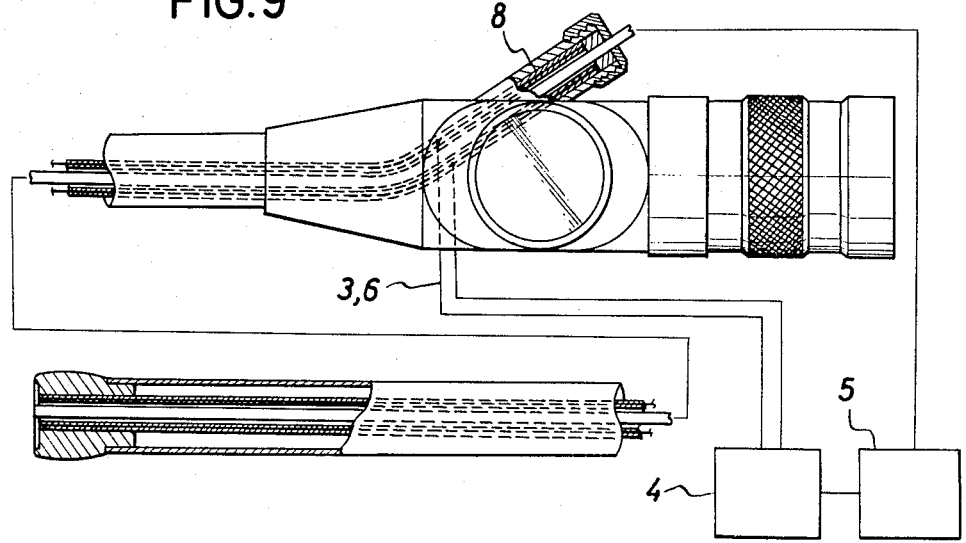

DEVICE FOR DETECTING A LEAK OF LASER

BACKGROUND OF THE INVENTION

A. Field of the Invention

The present invention relates to a device for securing the safety of an apparatus which makes use of the laser and an operator thereof, or more particularly, to a device for detecting a laser leak for electrically detecting a leakage of laser beam due to snapping of the laser guide which is provided for guiding the laser to a desired position.

B. Description of the Prior Art

A laser is a device which produces an intense, coherent directional beam of light by stimulating electronic, ionic or molecular transitions to lower energy levels. There are various kinds of laser, for example, gaseous laser such as a He-Ne laser, a solid laser such as a ruby laser and a YAG laser and a semiconductor laser such as a GaAs laser and these are widely applied in metal working, holography, or laser surgery. A laser guide comprising an optical fiber of a quartz fiber and a plastic coating of nylon thereon is used for guiding the laser beam from the laser source to a desired position such as a projector of the laser surgerical instrument. At first, a pilot beam of low-power range such as a gaseous laser is let in a laser guide in order to inspect the laser guide and the apparatus. After confirming the safety of the laser guide, the energized laser beam such as a YAG laser is let in to burn off a cancer or a polyp in a body cavity. But, there is still a possibility that the laser guide is snapped after the initial inspection. In that case, the energized laser beam leaks out to inflict harm upon the operator, patients and the apparatus itself. For this reason, leakage of the laser beam must be strictly detected.

SUMMARY OF THE INVENTION

The present invention aims at a device for electrically detecting the leakage of the laser beam due to snapping of the laser guide which is provided for guiding the laser beam to a desired position. A wire or a conductor which is connected to a detector is provided at the circumference of an optical fiber for a coating material of the laser guide. The snapping of the wire by melting or the variation of the resistance on account of the dielectric breakdown of the coating material is electrically detected by the detector.

The first object of the invention is to secure the safety of the apparatus, operator and the patients by stopping stimulation of the laser beam through strictly detecting leakage of laser beam from the laser guide.

The second object of the invention is to obtain a device for detecting the laser leak by which the safety confirmation of the pilot beam is compensated.

The above- and further objects and novel features of the invention will more fully appear from the following detailed description when the same is read in connection with the accompanying drawings. It is to be expressly understood, however, that the drawings are for purposes of illustration only and are not intended as a definition of the invention.

BRIEF DESCRIPTION OF THE DRAWINGS

FIG. 6 is a schematic cross-sectional view according to another embodiment of the invention in which a plurality of wires are opposed to each other in a suitable point of the coating material.

FIG. 7 is a schematic cross-sectional view according to another embodiment of the invention in which a conducting material is coated on the optical fiber.

FIG. 8 is a cross-sectional view of an example according to the present invention in which a wire is provided in a guide tube of a laser surgical instrument.

FIG. 9 is a cross-sectional view of an example according to the present invention in which a wire is provided in a forceps guide tube of an endoscope.

DETAILED DESCRIPTION OF PREFERRED EMBODIMENTS

Preferred embodiments according to the present invention will now be described herein-under with reference to FIGS. 1 to 7.

Figure 1:
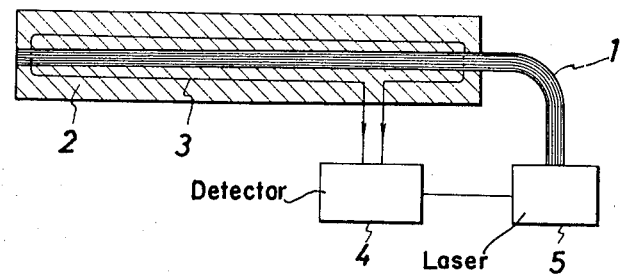
FIG. 1 is a schematic cross-sectional view according to an embodiment of the invention.
Figure 2:
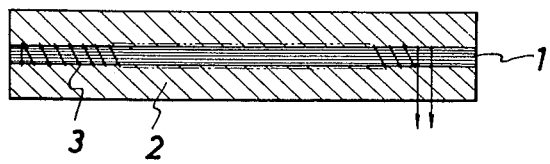
FIG. 2 is a schematic cross-sectional view in which a wire is wound around the optical fiber.
Figure 3:
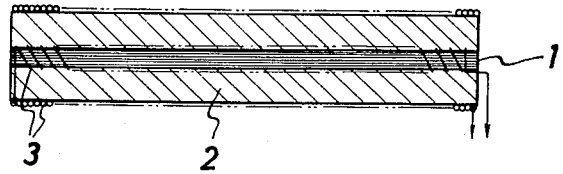
FIG. 3 is a schematic cross-sectional view according to another embodiment of the invention in which a wire is wound both around the optical fiber and the coating material.
Figure 4:
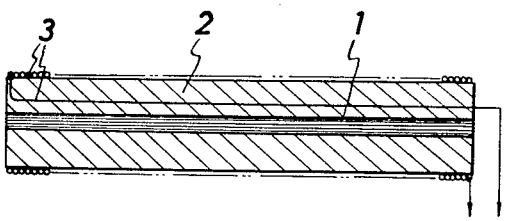
FIG. 4 is a schematic cross-sectional view according to another embodiment of the invention in which a wire wound around the coating material is further provided along the optical fiber.

In FIG. 1, numeral 1 indicates an optical fiber of quartz glass and so on, numeral 2 indicates a coating material of nylon, a laser guide being comprised by these components to guide a laser beam. Numeral 3 indicates a wire such as a fusible part of a fuse which is not only conductive but also fusible by the passage of an excess quantity of heat. The wire 3 is connected to an electrical detector 4 which controls a laser source 5. In FIG. 1, the wire 3 is provided in the coating material 2 along the optical fiber 1. In FIG. 2, the wire 3 is wound spirally around the optical fiber 1. In FIG. 3, the wire 3 is wound both around the optical fiber 1 and the coating material 2. In FIG. 4, the wire 3 spirally wound around the coating material 2 is further provided along the optical fiber 1.

By these provisions, when a laser beam leaks out of the laser guide on account of snapping, the wire 3 is melted by the energized laser beam. Consequently, an electric current in the wire 3 is cut off and then an electric signal is fed to the detector 4. On acceptance of the signal, the detector 4 detects the snapping of the laser guide and stops the stimulation of the laser source 5 or gives notice to an operator by an alarm not shown.

In the above-described embodiments, the electric signal is generated as a result of the melting of the wire 3. But, a wire, for example a nichrome wire, varies its resistance in response to temperature, thereby, the variation of resistance can be perceived by the detector 4. In this case, the slight leakage of the laser beam from the laser guide can strictly be perceived by the wire 3 in accordance with its temperature coefficient of resistance.

Figure 5:
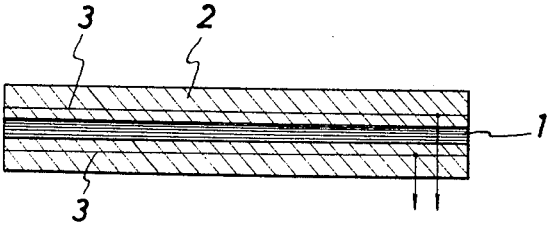
FIG. 5 is a schematic cross-sectional view according to another embodiment of the invention in which a plurality of wires are provided in the coating material.

In FIG. 5, a plurality of wires 3 of high conductivity such as a copper wire is provided along the optical fiber 1 in the coating material 2 and the wire 3 is connected to the detector 4. When the coating material 2 is melted by the leaked laser beam, a short circuit of the wire 3 takes place on account of the dielectric breakdown of the coating material 2 or when the insulation resistance of the coating material 2 varies, accordingly, an electric signal is generated to detect the short circuit or the variation of the resistance by the detector 4.

By these provisions, just like the foregoing embodiments, the leakage of the laser beam can strictly be detected. The plurality of wires 3 may be provided along the optical fiber 1 or, as shown in FIG. 6, the wire 3 may be opposed at a suitable points of the coating material.

The wires 3 are utilized in the above embodiments, but it is not of course necessary to use it so long as the conductivity is ensured. In FIG. 7, a conductive material 6 such as gold or copper is coated around the optical fiber 1 in order to detect the dielectric breakdown between said conductive material 6 and the wire 3 which is provided at the circumference of the coating material 2, or to detect the discontinuity of the conductive material 6 itself.

In the next place, examples will be described hereinunder in which the subject matter of the present invention is applied to a laser surgical instrument. The laser surgical instrument or so-called laser mess is a medical instrument for burning out a polyp or a cancer in a body cavity by an energized laser beam such as a YAG laser with the aid of an endoscope. It will be very harmful if the laser beam leaks out of the laser guide to burn out a point except the affected parts. For this reason, the above-said wire 3 or the conductive material 6 may be provided in the laser guide itself or, as shown in FIG. 8, the wire and/or the conductive material 6 may be provided in a guide tube 7 of the laser mess or, as shown in FIG. 9, in a forcep guide tube 8 which is used for guiding the laser mess so as to detect the leakage to secure the safety of said laser mess, the endoscope, the operator and patients.

As is described in detail, an accident caused by the energized laser beam can be prevented by the present invention through electrically detecting the leakage of the laser beam out of the laser guide as the discontinuity, the variation of resistance, the short circuit by the dielectric breakdown of the wire and/or the conducting material provided in the laser guide.

While there have been shown and described and pointed out the fundamental features of the invention as applied to preferred embodiments. It will be understood that the various omissions and substitutions and changes in the form and details of the mechanism illustrated and its operation may be made by those skilled in the art without departing from the spirit of the invention.

What is claimed is:

1. A laser guide suitable for insertion in a patient's body comprising an optical fiber formed of quartz glass and a plastic coating surrounding said optical fiber, a laser source optically coupled to one end of said optical fiber for supplying a laser beam to be carried by said guide, an electrical wire located adjacent and along a substantial portion of the length of said optical fiber, said wire forming a current loop with two ends, an electrical detector connected to said ends of said electrical wire for supplying current to said wire and for detecting changes in current flow through said wire, said detector being connected to said laser source to control the operation thereof, said electrical wire comprising an electrical material affected by the impingement of a laser beam so as to alter the current flowing therethrough, means for terminating the operation of said laser source when said detector detects an alteration of current flow through said electrical wire due to laser light escaping laterally of said fiber and impinging on said wire.

2. A device as set forth in claim 1, wherein said wire is spirally wound around said fiber optic means.

3. A device as set forth in claim 1, wherein said wire is spirally wound around both said fiber optic means and coating material.

4. A device as set forth in claim 1, wherein said wire is spirally wound around said coating and along said fiber optic means.

5. A device as set forth in claim 1, wherein said wire comprises a material which melts upon being hit by leaking laser beams to form an interruption in said electrical path.

6. A device as set forth in claim 1, wherein said electrical wire is embedded within said coating.

7. A device as set forth in claim 6, wherein said wire is located in said coating on opposite sides on said guide.

* * * * *